United States Patent
Van Weert et al.

(10) Patent No.: US 10,965,900 B2
(45) Date of Patent: Mar. 30, 2021

(54) SELF-SUSPENDED MONITOR

(71) Applicant: KONINKLIJKE PHILIPS N.V., Eindhoven (NL)

(72) Inventors: René Van Weert, Vught (NL); Marc Victor Arends, Best (NL)

(73) Assignee: KONINKLIJKE PHILIPS N.V., Eindhoven (NL)

(*) Notice: Subject to any disclaimer, the term of this patent is extended or adjusted under 35 U.S.C. 154(b) by 58 days.

(21) Appl. No.: 16/064,561

(22) PCT Filed: Dec. 23, 2016

(86) PCT No.: PCT/EP2016/082583
§ 371 (c)(1),
(2) Date: Jun. 21, 2018

(87) PCT Pub. No.: WO2017/109187
PCT Pub. Date: Jun. 29, 2017

(65) Prior Publication Data
US 2019/0007645 A1    Jan. 3, 2019

(30) Foreign Application Priority Data
Dec. 24, 2015   (EP) .................................... 15202689

(51) Int. Cl.
*H04N 5/645* (2006.01)
*F16M 11/42* (2006.01)
(Continued)

(52) U.S. Cl.
CPC ........... *H04N 5/645* (2013.01); *A61B 6/4435* (2013.01); *A61B 6/4464* (2013.01);
(Continued)

(58) Field of Classification Search
None
See application file for complete search history.

(56) References Cited

U.S. PATENT DOCUMENTS

| | | |
|---|---|---|
| 5,009,384 A | 4/1991 | Gerke et al. |
| 5,148,282 A | 9/1992 | Sedighzadeh |
(Continued)

FOREIGN PATENT DOCUMENTS

| | | |
|---|---|---|
| DE | 102009019358 A1 | 11/2010 |
| EP | 0920241 A2 | 6/1999 |
(Continued)

OTHER PUBLICATIONS

Philips User Manual 58-2014.
Philips Allura Xper FD Series—System Description and User Interfaces, Document version 8.2, 2014.

*Primary Examiner* — Heather R Jones

(57) ABSTRACT

The present invention relates to monitors. In order to facilitate mounting a monitor, a suspendable monitor (10) is provided for a ceiling suspended monitor system. The suspendable monitor comprises a video display (12), a structural frame (14), and a system interface (16). The video display is mounted to a front surface (18) of the structural frame. The system interface is mounted to the structural frame at one end and mountable to the ceiling suspended monitor system at the other end for suspending the suspendable monitor.

11 Claims, 5 Drawing Sheets

(51) Int. Cl.
  *F16M 13/02* (2006.01)
  *A61B 6/00* (2006.01)
  *F16M 11/22* (2006.01)
  *F16M 11/04* (2006.01)
  *H04N 5/655* (2006.01)

(52) U.S. Cl.
  CPC ............ *A61B 6/4494* (2013.01); *A61B 6/462* (2013.01); *F16M 11/043* (2013.01); *F16M 11/045* (2013.01); *F16M 11/22* (2013.01); *F16M 11/425* (2013.01); *F16M 13/027* (2013.01); *H04N 5/655* (2013.01); *A61B 6/4441* (2013.01); *A61B 6/4488* (2013.01)

(56) References Cited

U.S. PATENT DOCUMENTS

| | | |
|---|---|---|
| 7,077,373 B1 | 7/2006 | Hoebener |
| 7,224,373 B1 | 5/2007 | Duarte |
| 2003/0151701 A1 | 8/2003 | Sedighzadeh |
| 2008/0030939 A1* | 2/2008 | Gillespie ............... F16M 11/048 361/679.01 |
| 2009/0189050 A1 | 7/2009 | Ayadhi |
| 2010/0053455 A1* | 3/2010 | Kamada ............ G02F 1/133604 348/725 |
| 2012/0162878 A1 | 6/2012 | Fukuma |
| 2014/0217254 A1* | 8/2014 | Zhang .................. F16M 11/043 248/298.1 |
| 2016/0143602 A1 | 5/2016 | Hiroike |

FOREIGN PATENT DOCUMENTS

| | | |
|---|---|---|
| JP | 2003135404 A | 5/2003 |
| JP | 2012222112 A | 11/2012 |

\* cited by examiner

SELF-SUSPENDED MONITOR

CROSS-REFERENCE TO PRIOR APPLICATIONS

This application is the U.S. National Phase application under 35 U.S.C. § 371 of International Application No. PCT/EP2016/082583, filed on Dec. 23, 2016, which claims the benefit of European Patent Application No. 15202689.4, filed on Dec. 24, 2015. These applications are hereby incorporated by reference herein.

FIELD OF THE INVENTION

The present invention relates to the field of monitors and in particular to a suspendable monitor and to a ceiling suspended monitor system.

BACKGROUND OF THE INVENTION

In some applications or environments, such as in a clinical environment, like an interventional X-ray room, it may be required to mount a monitor to a ceiling e.g. for optimal viewing angle. To this end, monitor ceiling suspension frames have been developed for mounting a monitor e.g. via a VESA (Video Electronics Standards Association) interface. For example, U.S. Pat. No. 7,077,373 B1 describes a box-like frame for mounting a monitor. However, complexity may arise when mounting a monitor to a monitor ceiling suspension frame.

SUMMARY OF THE INVENTION

There may be a need to facilitate mounting a monitor.

The object of the present invention is solved by the subject-matter of the independent claims, wherein further embodiments are incorporated in the dependent claims. It should be noted that the following described aspects of the invention apply also for the suspendable monitor and for the ceiling suspended monitor system.

According to a first aspect of the present invention, a suspendable monitor is provided for a ceiling suspended monitor system. The suspendable monitor comprises a video display, a structural frame, and a system interface. The video display is mounted to a front surface of the structural frame. The system interface is mounted to the structural frame at one end and mountable to the ceiling suspended monitor system at the other end for suspending the suspendable monitor.

In this way, an integrated monitor and ceiling suspension frame is achieved with reduced number of parts. This may enable lower cost, simpler mounting and simpler logistics. In addition, there may be no or less obstruction of air flow due to the elimination of parts providing simplified heat management. Further, lower weight may be achieved due to elimination of redundant parts. This may enable spring arm constructions of the ceiling suspended monitor system. This may also provide a customer advantage, e.g. smaller footprint.

According to an example, the suspendable monitor further comprises a grip bar. The grip bar comprises a plurality of connection portions that are adapted for coupling with the structural frame and the video display on two opposite edges of the front surface of the structural frame.

With the grip bar, it is possible to position the integrated monitor and the grip bar may also protect the video display.

According to an example, the system interface is coupled to a topside of the structural frame.

The term "topside" relates to the top edge or top surface of the structural frame, i.e. the edge that faces upwards, i.e. towards the ceiling of a room.

In this way, a new interface is provided at top side of the integrated monitor. VESA interface may be removed.

According to an example, a utility box is provided to be mounted on the topside of the structural frame. The system interface is coupled to the utility box.

According to an example, the video display comprises a protection glass plate, a display panel, and a display electronics assembly. The protection glass plate and the display electronics assembly are mounted on opposite sides of the display panel. The display panel is coupled to the display electronics assembly and configured to receive video information and electrical power from the display electronics assembly.

The display electronics assembly may comprise e.g. PCB, power unit, digital converter, etc.

According to an example, a ventilation device is provided to be mounted on the structural frame.

The ventilation device may allow fresh air to enter and move through the monitor for heat management.

According to an example, the structural frame comprises a frame electronics assembly that comprises a power supply unit and/or a control unit for control of external devices.

According to an example, the structural frame further comprises an external interface on a rear surface opposite to the front surface. The external interface is adapted to be connected to a further system interface for mounting external devices to the monitor.

According to an example, the suspendable monitor is used in an X-ray imaging system. An X-ray indicator is provided on the suspendable monitor for indicating whether X-ray is in working.

According to an example, the suspendable monitor further comprises a rear cover. The rear cover is mounted on a rear surface of the structural frame, wherein the rear surface is opposite to the front surface.

The rear cover may be one piece that covers the full rear side and e.g. covers cabling.

According to an example, serviceable parts are accessible after removing the rear cover.

A user may remove the rear cover to replace or check serviceable parts.

According to an example, a cooling slot is provided on the rear cover.

According to a second aspect of the present invention, a ceiling suspended monitor system is provided for medical imaging. The ceiling suspended monitor system comprises a carriage and a suspendable monitor according to one of the examples described above and in the following. The carriage is movably mountable to a ceiling structure of a room. The system interface is mounted to the structural frame of the suspendable monitor at one end and mountable to the carriage at the other end for suspendably mounting the monitor to the carriage.

According to an aspect of the present invention, a suspendable monitor is provided that can be mounted without a monitor ceiling suspension frame. The suspendable monitor comprises a video display mounted on a structural frame, which is adapted for carrying other components, such as electronic components like a power supply unit and a control unit for controlling e.g. actuators, breaks of booms, etc. A system interface is mounted on the structural frame on one end. The other end of the system interface is mountable to e.g. a ceiling structure. Such integrated suspendable monitor may facilitate the mounting process.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the following drawings.

The figures are only schematically illustrated and not to scale. Same reference signs refer to same or similar features throughout the figures.

DETAILED DESCRIPTION OF EMBODIMENTS

Figure 1:
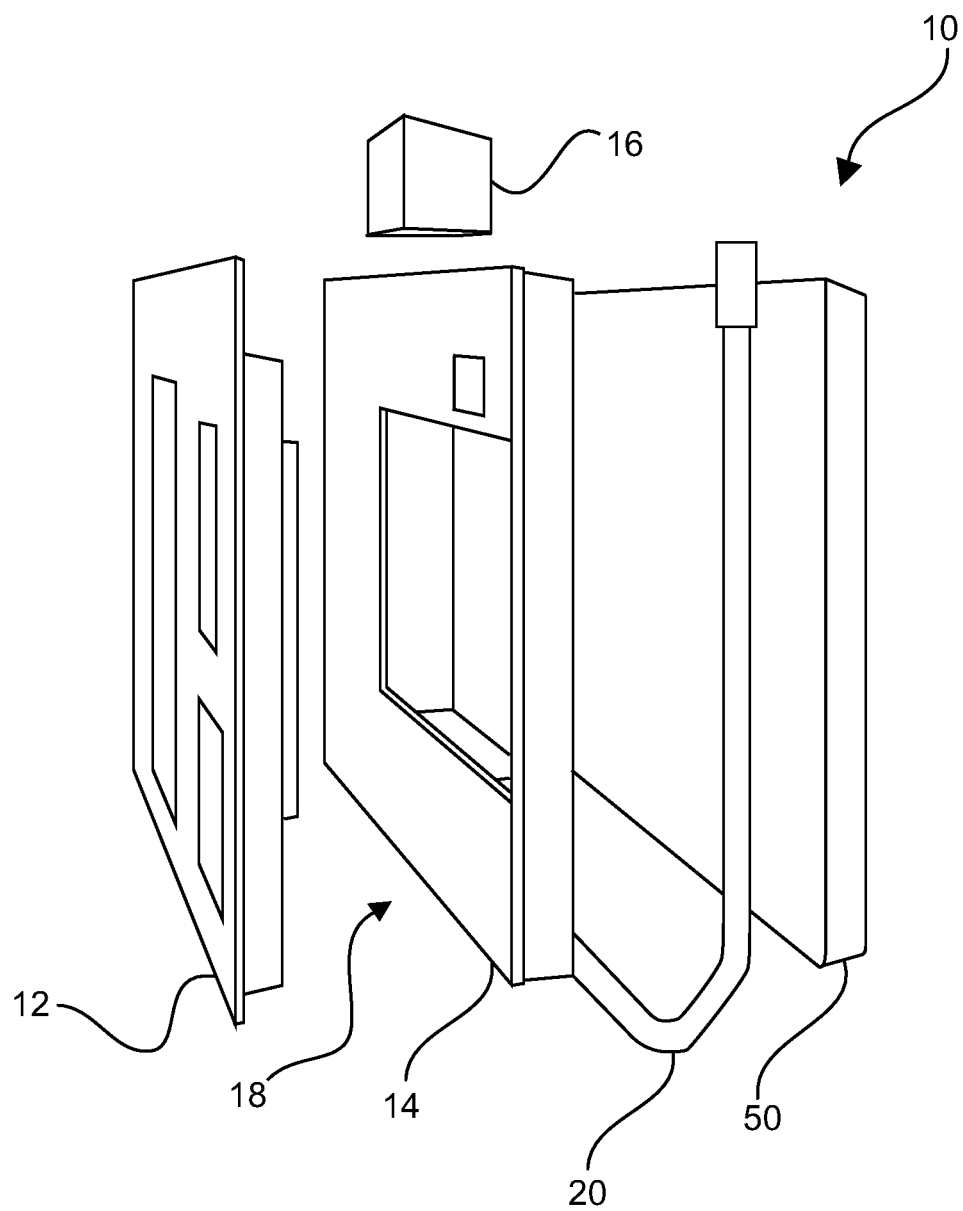
FIG. 1 shows an example of a suspendable monitor.

FIG. 1 shows an example of a suspendable monitor 10. The suspendable monitor 10 comprises a video display 12, a structural frame 14, and a system interface 16. The video display 12 is mounted to a front surface 18 of the structural frame 14. The system interface 16 is mounted to the structural frame 14 at one end and mountable to the ceiling suspended monitor system (not shown in FIG. 1) at the other end for suspending the suspendable monitor 10.

The system interface 16 may be coupled to a topside of the structural frame 14. In other words, a new interface is provided at topside of the integrated monitor. VESA interfaces may not be required.

Optionally, as shown in FIG. 1, the suspendable monitor 10 may further comprise a grip bar 20. The grip bar 20 comprises a plurality of connection portions 22 (see FIG. 4) that are adapted for coupling with the structural frame 14 and the video display 12 on two opposite edges of the front surface 18 of the structural frame 14.

In this way, an integrated monitor and ceiling suspension frame is achieved with reduced number of parts. Monitor ceiling suspension frames are no more needed for mounting the suspendable monitor to a ceiling.

Figure 2:
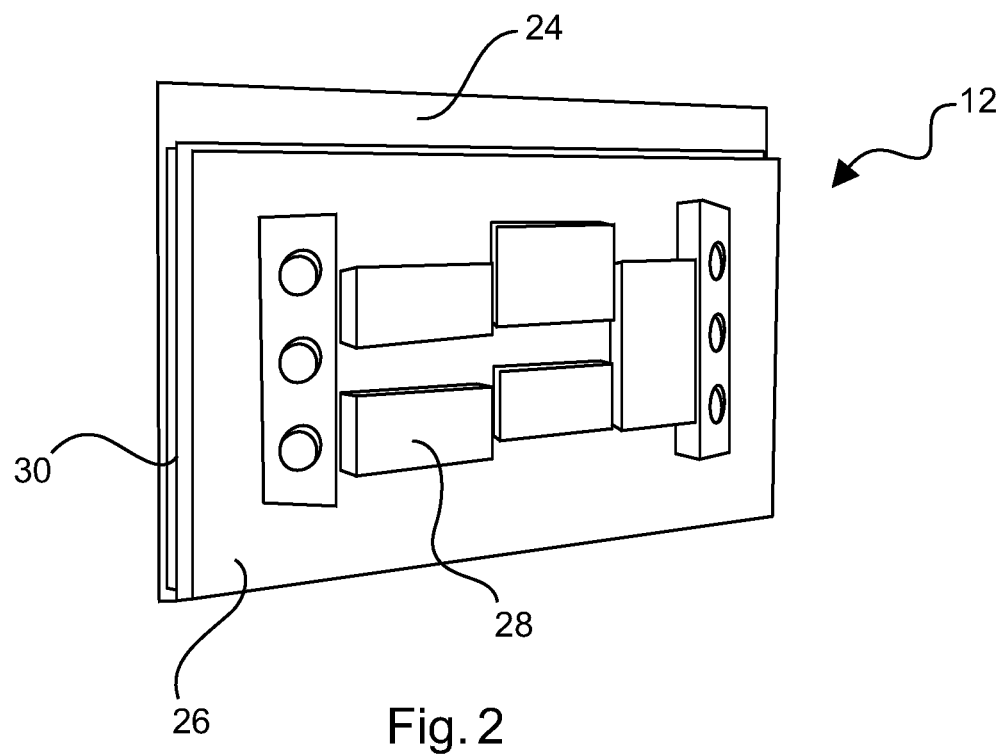
FIG. 2 shows an example of a video display.

FIG. 2 shows an example of the video display 12.

The video display 12 may comprise a protection glass plate 24, a display panel 26, and a display electronics assembly 28. The protection glass plate 24 and the display electronics assembly 28 are mounted on opposite sides of the display panel 26 in any appropriate method. In an example, shown as an option in FIG. 2, L profiles 30 are provided to be glued on the protection glass plate 24. The display panel 26 is mounted on the L-profiles 30.

The display electronics assembly 28 may relate to electronic components, such as printed circuit boards (PCBs), power unit, digital converter, etc., which may be mounted on the display panel 26 for providing power supply and video information.

An infrared (IR) sensor (not shown) may be provided to be mounted e.g. on the display panel 26 or on the structural frame 14 for receiving control signals, which may contain commands that may enable selection and handling of images.

Figure 3:
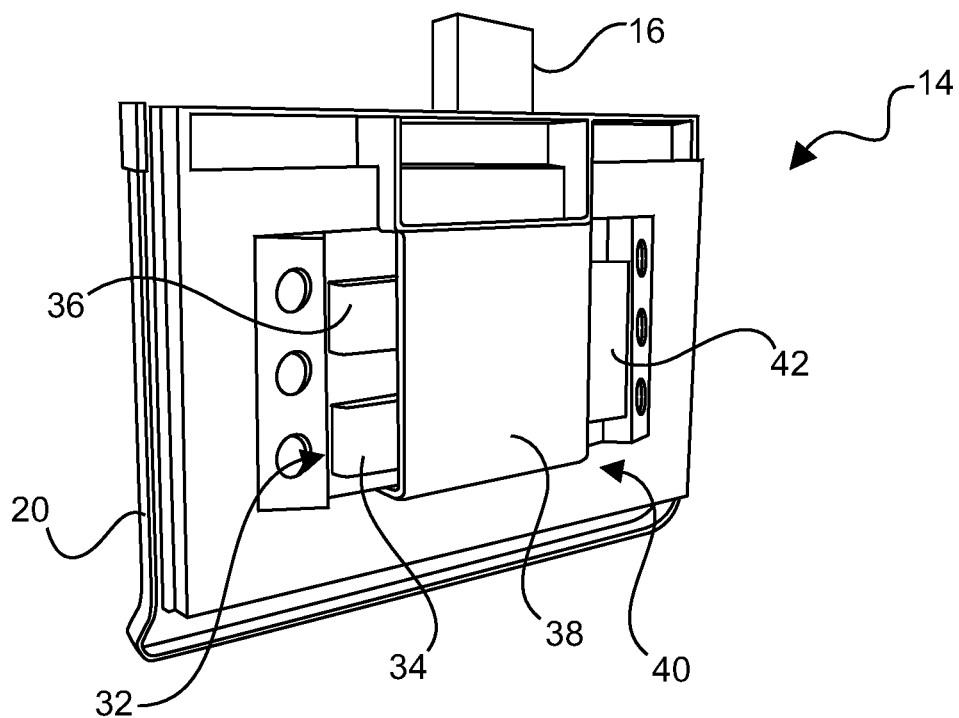
FIG. 3 shows an example of a structural frame.

FIG. 3 shows an example of the structural frame 14, which is provided to carry all components.

The structural frame 14 may comprise a frame electronics assembly 32, which comprises a power supply unit 34 and/or a control unit 36 for control of external devices.

Examples of external devices may include e.g. actuators, breaks of booms, etc. With actuators for example, the control unit 36 can be used to control and adjust the position and/or orientation of the suspendable monitor 10 when mounted on a ceiling suspended monitor system for optimal viewing angle.

The structural frame 14 may optionally comprise an external interface 38 on a rear surface 40 opposite to the front surface 18. The external interface 38 is adapted to be connected to a further system interface (not further shown) for mounting external devices to the monitor.

As a further option, a ventilation device 42 is provided to be mounted on the structural frame 14. The ventilation device 42 may be a fan, which accelerates the air flow for heat management.

The structural frame 14 may also have grip fixations to be coupled to the grip bar 20.

Figure 4:
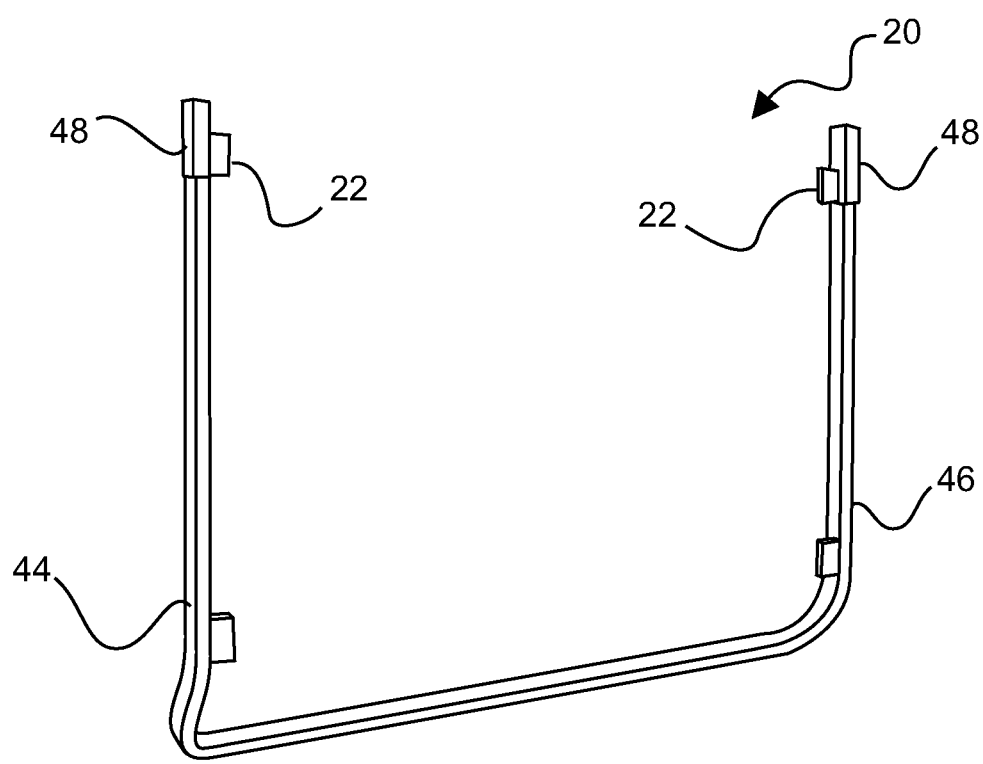
FIG. 4 shows an example of a grip bar.

FIG. 4 shows an example of the grip bar 20. The grip bar 20 has a U-shape with two arms 44, 46 adapted to be coupled to the structural frame 14 via the connection portions 22. For example, the grip bar 20 in FIG. 4 comprises four connection portions 22. Each arm 44, 46 is provided with two connection portions 22.

In a further example (not shown), two grip bars are provided, e.g.: left grip bar and right grip bar. Each grip bar has two or more connection portions for coupling with the structural frame and the video display.

As an option, when the suspendable monitor 10 is used in an X-ray imaging system, an X-ray indicator may be provided on the suspendable monitor for indicating whether X-ray is in working.

In an example, shown as an option in FIG. 4, the X-ray indicator 48 is provided on the grip bar 20. In a further example (not further shown), the X-ray indicator 48 is provided on the system interface 16.

The grip bar 20 may be used to position the integrated suspendable monitor 10 and protect the protection glass plate 24 and the display panel 26.

Figure 5:
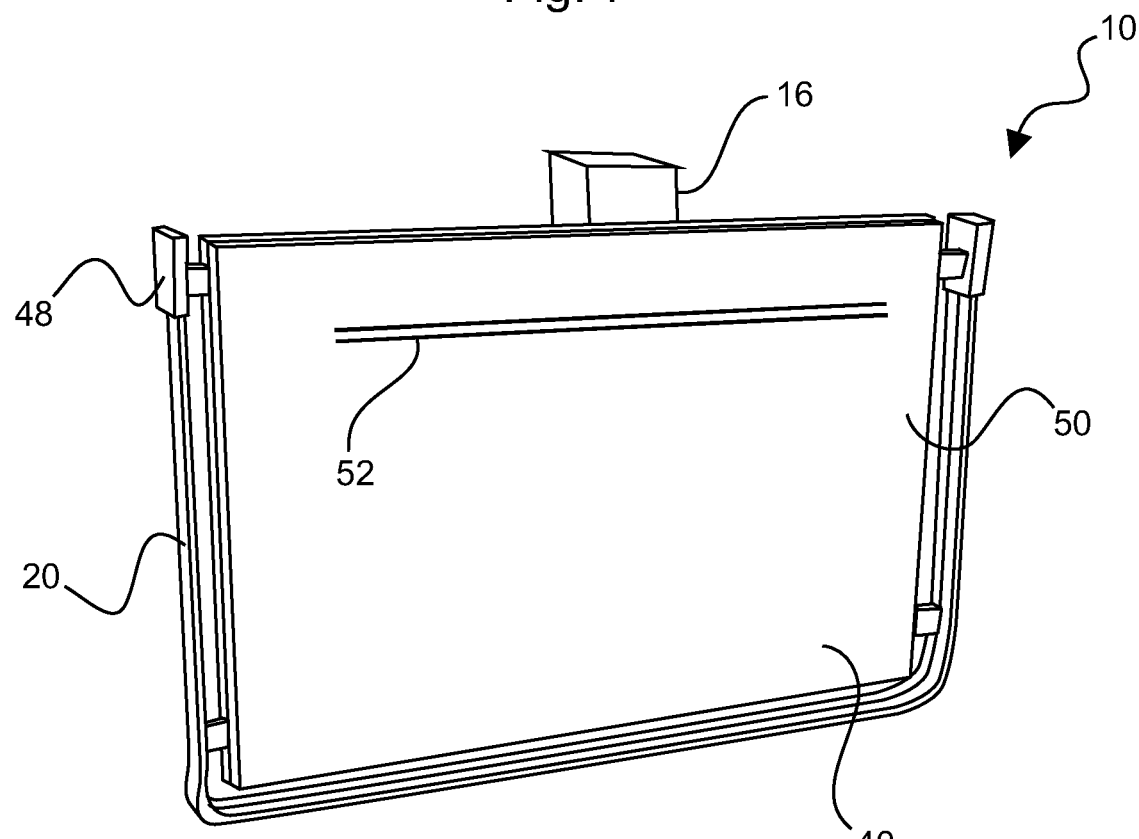
FIG. 5 shows a further example of a suspendable monitor.

FIG. 5 shows an example of the suspendable monitor 10, which comprises a rear cover 50. The rear cover 50 is mounted on the rear surface 40.

The rear cover 50 may be one piece that covers the full rear side and e.g. covers cabling and PCBs.

As a further option, serviceable parts (not shown) are assessable after removing the rear cover 50. This may facilitate replacing or checking serviceable parts.

Also shown as an option in FIG. 5, a cooling slot 52 is provided on the rear cover 50 for heat management. Multiple cooling slots may be provided, if necessary.

Figure 6:
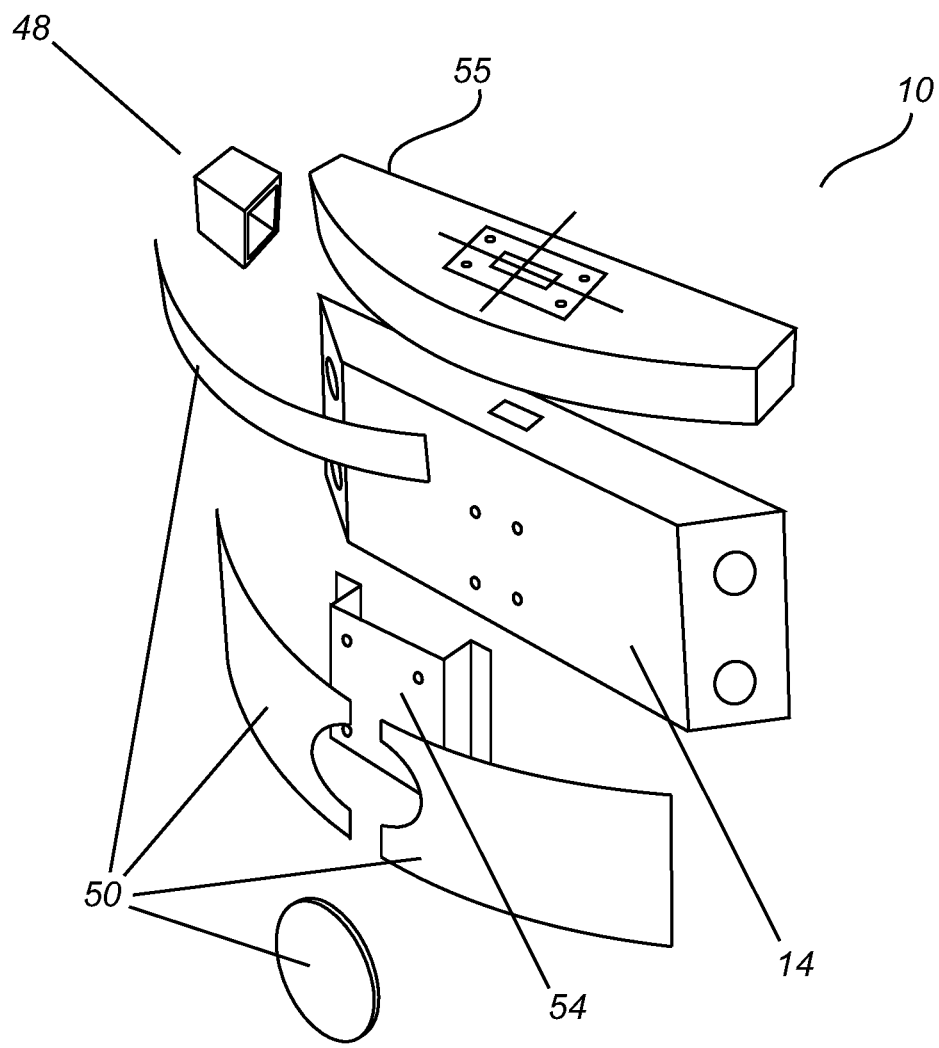
FIG. 6 shows another example of a suspendable monitor.

FIG. 6 shows a further example of the suspendable monitor 10, which has the rear cover 50 made of multiple pieces. A third party interface 54 is provided that allows any third party equipment to be mounted to the suspendable monitor. The third party interface may be e.g. a VESA standard interface.

Further, a utility box 55 may be provided to be mounted on the topside of the structural frame 14 (not further shown). The system interface 16 is coupled to the utility box 55. The system interface 16 may be adapted for carrying cables for connecting the utility box 55 for providing e.g. power supply and/or transmitting video signals.

Figure 7:
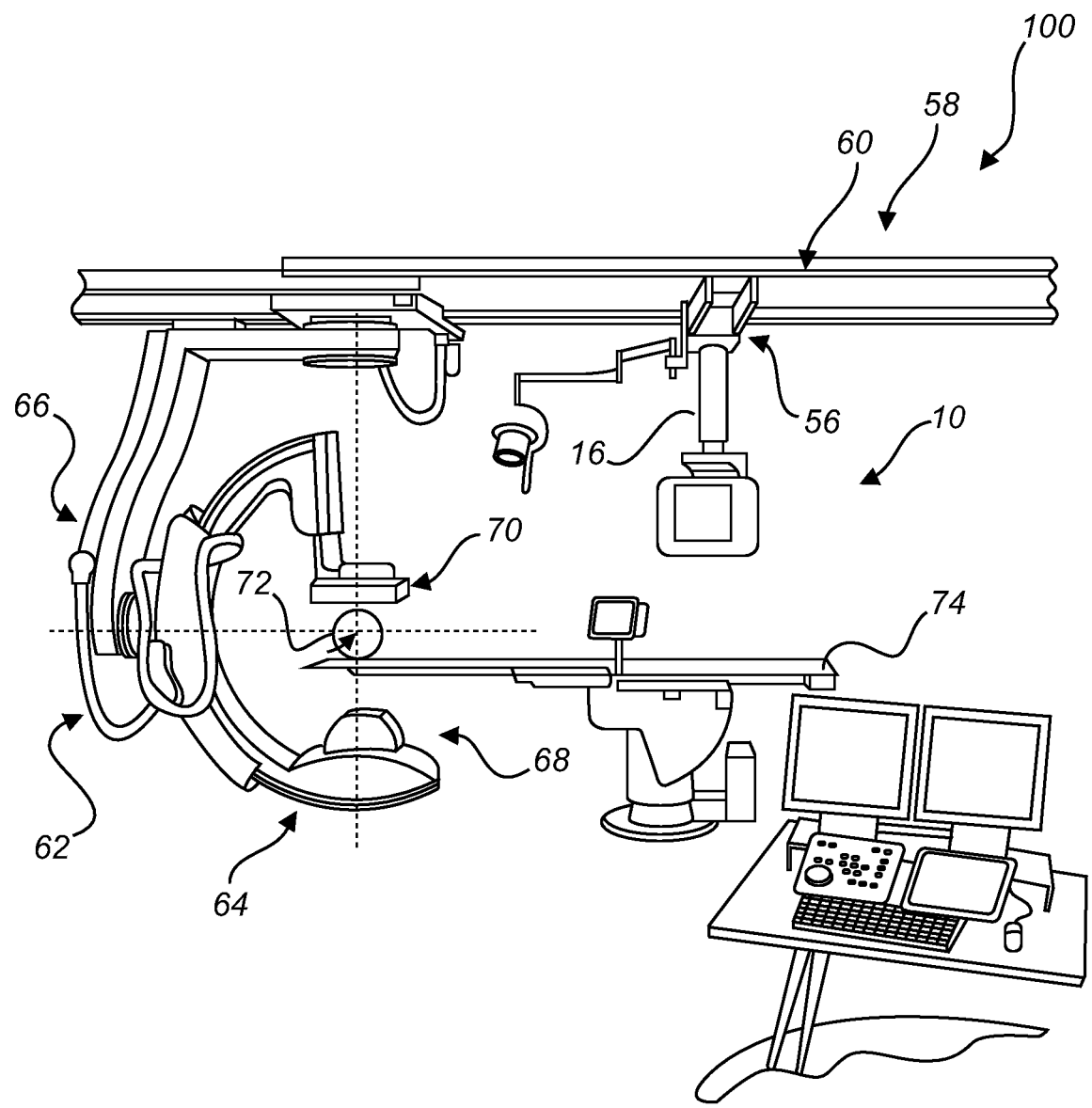
FIG. 7 shows an example of a ceiling suspended monitor system.

FIG. 7 shows a ceiling suspended monitor system 100 for medical imaging. To facilitate explanation of the present techniques, an X-ray imaging system in form a C-arm scanner will be generally discussed herein, though it is to be understood that non-X-ray implementations are also within the scope of the present techniques.

The system comprises a carriage 56 and the suspendable monitor 10 according to one of the above-mentioned examples. The carriage 56 is movably mountable to a ceiling structure 58 e.g. via a rail arrangement 60. The system interface 16 is mounted to the structural frame 14 (not further shown) at one end and mountable to the carriage 56 at the other end for suspendably mounting the suspendable monitor 10 to the carriage 56.

In this way, the suspendable monitor can be mounted on the ceiling structure 58 directly without the need of a separate monitor ceiling suspension frame, thus facilitating the mounting process.

The suspendable monitor 10 may also be provided with height adjustment for translating the suspendable monitor in a vertical direction. As a further option, the suspendable monitor 10 may also be configured to be rotationally adjustable. The height adjustment and rotation adjustment may be controlled by the control unit 36 (see FIG. 3) mounted on the structural frame 14.

This may allow flexible, freely translating and rotating positioning for optimal viewing angle.

Also illustrated in FIG. 7 is a rotational C-arm scanner 62 with a C-arm 64 and an L-arm 66. The L-arm 66 is attached to the ceiling structure 58 via the rail arrangement 60.

An X-ray source 68 and an X-ray detector 70 are mounted on the C-arm 64. The C-arm 64 can perform a "roll movement" about an axis of the C-arm 64 for imaging a subject 72 on a patient support 74.

Images acquired by the X-ray detector 70 or from other sources may be displayed on the suspendable monitor 10.

It has to be noted that embodiments of the invention are described with reference to different subject matters. In particular, some embodiments are described with reference to monitor claims whereas other embodiments are described with reference to the system claim. However, a person skilled in the art will gather from the above and the following description that, unless otherwise notified, in addition to any combination of features belonging to one subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A suspendable monitor for a ceiling suspended monitor system, comprising:
    a video display;
    a structural frame;
    a system interface; and
    a grip bar to enable a user to grasp and position the suspendable monitor and to protected the mounted video display,
    wherein the video display is mounted to a front surface of the structural frame;
    wherein the system interface is mounted, at one end, to a topside of the structural frame, and mountable, at another end, to the ceiling suspended monitor system for suspending the suspendable monitor, and
    wherein the grip bar comprises a pair of side portions extending along two opposite edges of the front surface of the structural frame, a lower grip portion connecting the lower ends of the side portions and extending forwardly to protrude past a front surface of the video display, and a plurality of connection portions that are adapted for coupling the side portions of the grip bar with the structural frame and the video display on two opposite edges of the front surface of the structural frame, whereby the side portions of the grip bar are positioned to protect the video display from side impacts to the video display, and the lower grip portion of the grip bar both protects the bottom of the video display from bottom impacts and presents a user with a structural component to grasp when positioning the suspendable monitor.

2. The suspendable monitor according to claim 1, wherein a utility box is provided to be mounted on the topside of the structural frame; and
    wherein the system interface is coupled to the utility box.

3. The suspendable monitor according to claim 1, wherein the video display comprises:
    a protection glass plate;
    a display panel; and
    a display electronics assembly;
    wherein the protection glass plate and the display electronics assembly are mounted on opposite sides of the display panel; and
    wherein the display panel is coupled to the display electronics assembly and configured to receive video information and electrical power from the display electronics assembly.

4. The suspendable monitor according to claim 3, wherein a ventilation device is provided to be mounted on the structural frame.

5. The suspendable monitor according to claim 3, wherein the structural frame comprises a frame electronics assembly that comprises:
    a power supply unit; and/or
    a control unit for control of external devices.

6. The suspendable monitor according to claim 5, wherein the structural frame further comprises an external interface on a rear surface opposite to the front surface; and
    wherein the external interface is adapted to be connected to a further system interface for mounting external devices to the monitor.

7. The suspendable monitor according to claim 6, wherein the suspendable monitor is used in an X-ray imaging system; and
    wherein an X-ray indicator is provided on the suspendable monitor for indicating whether X-ray is in working.

8. The suspendable monitor according to claim 1, wherein the suspendable monitor further comprises:
a rear cover;
  wherein the rear cover is mounted on a rear surface of the structural frame, wherein the rear surface is opposite to the front surface.

9. The suspendable monitor according to claim 8, wherein serviceable parts are accessible after removing the rear cover.

10. The suspendable monitor according to claim 8, wherein a cooling slot is provided on the rear cover.

11. A ceiling suspended monitor system for medical imaging, comprising:
a carriage; and
a suspendable monitor according to claim 8;
  wherein the carriage is movably mountable to a ceiling structure of a room; and
  wherein the system interface is mounted, at one end, to the structural frame of the suspendable monitor, and mountable, at an other end, to the carriage for suspendably mounting the suspendable monitor to the carriage.

* * * * *